United States Patent [19]

Hagen et al.

[11] Patent Number: 4,736,062

[45] Date of Patent: Apr. 5, 1988

[54] PROCESS FOR PREPARING METHACRYLIC ACID

[75] Inventors: Gary P. Hagen, Glen Ellyn; Thomas G. Smith, Naperville, both of Ill.

[73] Assignee: Amoco Corporation, Chicago, Ill.

[21] Appl. No.: 624,050

[22] Filed: Jun. 25, 1984

[51] Int. Cl.[4] .................. C07C 51/353; C07C 51/377; C07C 57/04; C07C 57/065

[52] U.S. Cl. ...................... 562/599; 203/15; 203/68; 203/69; 203/70; 203/DIG. 21; 260/404.5; 568/485; 568/493

[58] Field of Search ...................... 562/599; 260/405.5

[56] References Cited

U.S. PATENT DOCUMENTS

| | | | |
|---|---|---|---|
| 3,414,485 | 12/1968 | Speed | 562/600 |
| 3,830,707 | 8/1974 | Kageyama et al. | 562/600 |
| 4,040,913 | 8/1977 | Clovis et al. | 562/600 |

FOREIGN PATENT DOCUMENTS 721773  11/1965  Canada .................................. 562/599

OTHER PUBLICATIONS

Hougen et al., Chemical Process Principles, Part III, Kinetics and Catalysis, John Wiley & Sons, Inc., N.Y., 1947, pp. 1031–1032.

*Primary Examiner*—Vivian Garner
*Attorney, Agent, or Firm*—James R. Henes; William H. Magidson; Ralph C. Medhurst

[57] ABSTRACT

A process is disclosed for producing an alpha-, beta-ethylenically unsaturated monocarboxylic acid compound which comprises the aldol-type condensation of a saturated aliphatic monocarboxylic acid compound under vapor phase conditions in the presence of a hydrocarbon of 6 to 12 carbon atoms and a solid catalyst.

5 Claims, No Drawings

PROCESS FOR PREPARING METHACRYLIC ACID

FIELD OF THE INVENTION

In general, the field of this invention relates to a method of reacting in the vapor phase a saturated aliphatic monocarboxylic acid compound and formaldehyde, the reaction product stream comprising unreacted saturated aliphatic monocarboxylic acid compound, an alpha, betaethylenically unsaturated aliphatic monocarboxylic acid compound of one more carbon atom than the starting saturated aliphatic monocarboxylic acid compound, water, unreacted formaldehyde and by-products. The reaction is in the presence of a silica catalyst and a $C_6$ to $C_{12}$ hydrocarbon. Surprisingly, it has been found that introduction of a $C_6$ to $C_{12}$ hydrocarbon into the reactor increases yield of the alpha-beta-unsaturated aliphatic monocarboxylic acid compound.

In more specific terms, the field of this invention relates to a process for preparing methacrylic acid from formaldehyde and propionic acid in an improved yield, based on propionic acid, without any increased loss of reactants to by-products, in the presence of a silica catalyst and a $C_6$ to $C_{12}$ hydrocarbon. The process is a vapor phase aldol-type condensation of propionic acid and formaldehyde wherein the products are methacrylic acid, water and by-products. Unreacted propionic acid, and unreacted formaldehyde are present in the process effluent.

BACKGROUND OF THE INVENTION

Unsaturated acids, such as methacrylic and acrylic acids, acrylonitrile, and the esters of such acids, such as methyl methacrylate, are widely used for the production of corresponding polymers, resins and the like. Various processes and catalysts have been proposed for the conversion of alkanoic acids, such as acetic acid or propionic acid, and formaldehyde to the corresponding unsaturated monocarboxylic acids, e.g., methacrylic acid, by an aldol-type reaction. Generally, the reaction of a carboxylic acid and formaldehyde takes place in the vapor or gas phase while in the presence of a basic or acidic catalyst.

The literature is replete with disclosures of the reaction of aliphatic carboxylic acid compounds with formaldehyde to produce alpha, beta-ethylenically unsaturated aliphatic monocarboxylic acid compounds of one more carbon atom than in the saturated carboxylic acid. For every molecule of alpha, beta-ethylenically unsaturated aliphatic monocarboxylic acid produced there is one molecule of water by-product. It is necessary to separate the alpha, beta-ethylenically unsaturated carboxylic acid compound, formaldehyde and the starting unsaturated carboxylic acid.

In the case of methacrylic acid, this means that the methacrylic acid must be separated from propionic acid, formaldehyde and water. This separation presents several problems since each of the components are water soluble and because propionic acid and methacrylic acid have boiling points that are so close that it is difficult to fractionate one from the other. Further, the separation is complicated by the fact that methacrylic acid has a tendency to homopolymerize, and formaldehyde, if water is removed from the system, also has a tendency to homopolymerize.

Of the various alpha. beta-ethylenically unsaturated compounds, it is generally recognized that methacrylic acid has one of the greatest tendencies to polymerize and it is extremely difficult to handle at elevated temperatures. In this regard, we have found that the presence of certain reaction by-products greatly increase the propensity of methacrylic acid to homopolymerize. Specifically, alpha-, beta- unsaturated ketones, i.e., ethylisopropenyl ketone and 2,5-dimethylcyclopenten-1-one, have been shown to greatly increase the degree of methacrylic acid homopolymerization. Additionally, methacrylic acid, propionic acid and formaldehyde individually form binary azeotropes with water. The boiling points of the three binary azeotropes are within 1° F. of each other and are thus exceedingly difficult to separate.

The following table lists boiling points and weight percentages of binary azeotropes of water and methacrylic acid, propionic acid and formaldehyde at 760 mm Hg.

|  | Wt % | Wt % $H_2O$ | B.P. °F. |
| --- | --- | --- | --- |
| Methacrylic acid | 23.1 | 76.9 | 210.7 |
| Propionic acid | 17.8 | 82.2 | 210.4 |
| Formaldehyde | 18.25–21.0 | 79.0–81.75 | 210.4 |

In somewhat greater detail, the invention relates to a process for an aldol-type condensation of a saturated aliphatic monocarboxylic acid compound and an aldehyde wherein said monocarboxylic acid is propionic acid and said aldehyde is formaldehyde. As is well-known, an aldol-type condensation can be base-catalyzed and is subject to ready dehydration if the $\beta$-hydroxyl group is adjacent to an $\alpha$-hydrogen atom. The product is an $\alpha, \beta$-unsaturated acid of one more carbon atom than the original unsaturated aliphatic monocarboxylic acid, when the reacting aldehyde is formaldehyde. The reaction using propionic acid and formaldehyde is:

$$CH_3CH_2COOH + HCHO$$
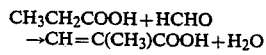
$$\rightarrow CH=C(CH_3)COOH + H_2O$$

While the prior art has indicated that it is possible to carry out these reactions utilizing various catalysts, none of these references disclose specifically the use of a silica catalyst comprising at least one cation of a Group I or Group II metal and a silica support wherein the cation is present in a concentration of 0.001 to 0.2 equivalents per 100 grams silica support on a dry solids basis in the presence of a $C_6$ to $C_{12}$ hydrocarbon.

A careful review of the prior art has failed to disclose any examples wherein addition of a $C_6$ to $C_{12}$ hydrocarbon to the aldol-type condensation reaction improved the product yield.

In the prior art a number of methods which use solvent materials have been taught to separate the unreacted propionic acid and unreacted formaldehyde from the aqueous effluent resulting from vapor phase condensation of propionic acid and formaldehyde. U.S. Pat. No. 3,414,485 teaches use of a selective organic solvent to recover methacrylic acid from an aqueous reaction product effluent. Suitable organic solvents include o-, m- and p-xylene, toluene, n-octane, mono-chlorobenzene, methylamylketone, ligroin and methyl methacrylate monomer. U.S. Pat. No. 3,478,093 teaches use of a lactam having 4 to 7 ring members and a hydrocarbon radical substituent on the nitrogen atom as an extraction solvent to separate methacrylic acid from aqueous mixtures. U.S. Pat. No. 3,781,332 teaches use of a dual mixture containing methyl or ethyl methacrylate and not more than 50% of xylene, ethyl benzene or a mixture thereof. U.S. Pat. No. 4,040,913 teaches a decantation method wherein an organic solvent extracts methacrylic acid and azeotropes with propionic acid. The aqueous raffinate is separated by decantation. U.S. Pat. No. 4,142,058 teaches use of a mixed solution of methyl methacrylate and toluene to separate methacrylic acid from an aqueous solution containing acetic acid. U.S. Pat. No. 4,147,721 teaches use of methyl n-propyl ketone as a solvent to recover methacrylic acid from an aqueous reaction product.

However, introduction of a $C_6$ to $C_{12}$ hydrocarbon into the reactor to increase reaction yield has not been previously taught. Preferably the $C_6$ to $C_{12}$ hydrocarbon azeotropes with propionic acid to permit separation of propionic acid from methacrylic acid by downstream distillation.

The general object of this invention is to provide an improved method of reacting a saturated monocarboxylic acid compound, with formaldehyde to obtain an increased yield of an alpha, beta-ethylenically unsaturated aliphatic monocarboxylic acid compound of one more carbon atom than the starting saturated monocarboxylic acid compound. A more specific object of this invention is to provide an improved method of preparing methacrylic acid from propionic acid and formaldehyde which results in an increased yield of the desired methacrylic acid.

The general object of this invention can be attained by injecting a $C_6$ to $C_{12}$ hydrocarbon into the reaction of a saturated aliphatic monocarboxylic acid compound, and a formaldehyde compound in the presence of a catalyst comprising a silica support and at least one cation of a Group I or Group II metal in a concentration of about 0.001 to 0.2 cation equivalents per 100 grams by weight silica support on a dry solids basis at a temperature of from about 280° C. to about 500° C. under vapor phase conditions. Yields have increase by about 10% (e.g., 30% to 33%). Suitable $C_6$ to $C_{12}$ hydrocarbons are substantially non-reactive, water-immiscible compounds capable of breaking a water azeotrope of saturated aliphatic carboxylic acid compound. In a preferred method of operation, upon distillation, a major proportion of the ethylenically unsaturated monocarboxylic acid compound remains in the bottom of the column, and a major portion of the water, a portion of the formaldehyde compound and a major portion of the $C_6$ to $C_{12}$ hydrocarbon are removed overhead. In separation of the reaction products of propionic acid and formaldehyde in the production of methacrylic acid and water using a silica catalyst, we have found it advantageous to recycle the recovered $C_6$–$C_{12}$ hydrocarbon through the reactor. We have also found that by removing a side stream below the top of the distillation column, it is possible to recycle a substantial portion of unreacted formaldehyde and propionic acid together with the hydrocarbon to the reactor and avoid the polymerization and plugging of the distillation column by polymerized formaldehyde as is pointed out in application Ser. No. 624,049, Pat. No. 4,599,144, filed on even date in the names of Baleiko, et al, incorporated herein by reference. In a more preferred method of operation, the unreacted propionic acid, formaldehyde and $C_6$ to $C_{12}$ hydrocarbon are recycled to the inlet ports of the reactor and employed to produce methacrylic acid.

SUMMARY OF THE INVENTION

A method is disclosed of reacting a saturated aliphatic monocarboxylic acid compound and a formaldehyde compound, the reaction products comprising saturated aliphatic monocarboxylic acid compound, alpha, beta-ethylenically unsaturated aliphatic monocarboxylic acid compound of one more carbon atom than the starting saturated aliphatic monocarboxylic acid compound, water and by-products. The process comprises adding to the reactor a $C_6$ to $C_{12}$ hydrocarbon. Preferably the $C_6$ to $C_{12}$ hydrocarbon is a substantially non-reactive compound capable of breaking or preventing the formation of a water azeotrope of said saturated aliphatic monocarboxylic acid compound. In a preferred method of operation, said reaction products are fractionally distilled together with said substantially non-reactive compound under conditions whereby (1) a major proportion of the ethylenically unsaturated monocarboxylic acid compound remains in the bottom of the distillation column, (2) a major portion of the water, a portion of the formaldehyde compound and a major portion of the compound capable of breaking or preventing the formation of said azeotrope are removed overhead. In a more preferred method of operation, a side stream is removed below the top of the distillation column comprising water, a major portion of formaldehyde, and a substantial proportion of saturated aliphatic monocarboxylic acid. The non-reactive compound is recovered and recycled through the reactor.

DESCRIPTION AND PREFERRED EMBODIMENTS OF THE INVENTION

The process of this invention will be understood from the following description and examples.

The process of this invention is a process for the preparation in improved yield of alpha-, beta-ethylenically unsaturated monocarboxylic compounds of one more carbon atom than the starting saturated aliphatic monocarboxylic acid compound. Particularly it is a process for preparation in improved yield of methacrylic acid from propionic acid and formaldehyde wherein a $C_6$ to $C_{12}$ hydrocarbon is added to the reactor, thereby increasing yield to methacrylic acid, based on propionic acid.

It is not known at this time why addition of a $C_6$ to $C_{12}$ hydrocarbon to the reaction of propionic acid and formaldehyde to produce methacrylic acid in the presence of a silica catalyst improves the yield. However, it is postulated that the presence of the $C_6$ to $C_{12}$ hydrocarbon aids the reaction by desorbing one or more of the reaction components or products from the catalyst. It is considered that the success of this method of preparing methacrylic acid in increased yield is due primarily to the use of particular process conditions, specifically a silica catalyst and use of a suitable $C_6$ to $C_{12}$ hydrocarbon.

In a preferred method of operation, addition of a suitable $C_6$ to $C_{12}$ hydrocarbon to the reactor breaks or prevents the formation downstream of a propionic/water azeotrope. Upon distillation of reactor effluent, the unreacted propionic acid in the distillation tower is capable of being removed in a sidestream. This sidestream typically contains 60–95 (wt) % of the unreacted formaldehyde and 10–70 (wt) % of the unreacted propionic acid entering the distillation column, and up to no more than a total about 50 (wt) % water and methacrylic acid. The sidestream is suitable for direct recycle to the methacrylic acid synthesis reactor. The recycle of large percentages of unreacted formaldehyde and unreacted propionic acid directly back to the synthesis reactor reduces need for recovery of formaldehyde and propionic acid downstream and downsizes recovery equipment. Immediate recovery and recycle of unreacted formaldehyde and unreacted propionic acid immediately back to the synthesis reactor is an economic advantage.

Because the product effluent stream contains amounts of unreacted propionic acid and unreacted formaldehyde as well as water, selection of a suitable hydrocarbon in a preferred method of operation wherein reactor effluent is distilled to separate the components is determined by the boiling points of azeotropes of propionic acid and methacrylic acid. Both propionic acid and methacrylic acid form water azeotropes which boil at approximately 99° C. Separation by distillation of the $C_6$ to $C_{12}$ hydrocarbon in the presence of water requires that the water:hydrocarbon azeotrope which forms have a boiling point below the boiling points of the propionic acid and methacrylic acid water azeotropes. Preferably, the boiling point of the water:hydrocarbon azeotrope be no more than 95° C.

Boiling points at atmospheric pressure of preferable hydrocarbon:water azeotropes are:

| Hydrocarbon | % Water | B.P.°C. |
|---|---|---|
| n-Hexane | 5 | — |
| n-Heptane | 13 | 79 |
| n-Octane | 23 | 90 |
| n-Nonane | 40 | 95 |

Branched $C_6$ to $C_{12}$ saturated aliphatic hydrocarbons, aromatic hydrocarbons of 6 to 12 carbon atoms, cycloalkanes of 6 to 12 carbon atoms, and mixtures thereof which form water:hydrocarbon azeotropes with boiling points of no more than 95° C. can also be preferred.

A large number of catalysts, both water-tolerant and water-intolerant types, exhibit activity in the aldoltype condensation reaction of this invention. Specific catalyst materials that are useful in the process include synthetic alkali metal aluminosilicates, natural alkali metal aluminosilicates, synthetic alkaline earth metal aluminosilicates, natural alkaline earth metal aluminosilicates, alkali metal hydroxides on synthetic aluminosilicates, alkali metal hydroxides on natural aluminosilicates, alkaline earth metal hydroxides on synthetic aluminosilicates, alkali metal hydroxides on silica gel, alkaline earth metal hydroxides on silica gel, sodium silicate on silica gel, potassium silicate on silica gel, molybdenum oxide on silica gel, silica gel, synthetic manganese aluminosilicate, natural manganese aluminosilicate, synthetic cobalt aluminosilicate, natural cobalt aluminosilicate, synthetic zinc aluminosilicate, and natural zinc aluminosilicate.

Catalyst compositions found to be especially useful in the reaction to form methacrylic acid from propionic acid and formaldehyde are the subject of applications numbered Ser. No. 624,040 and Ser. No. 624,041 filed an even date in the names of Hagen, et al, and Kaduk, et al, respectively, which are hereby incorporated by references.

The synthesis reactor feed stock should be composed of propionic acid, formaldehyde, and some water. The mole ratio of propionic acid to formaldehyde should be maintained within the range from about 25/1 to about 1/25; with a preferred range of about 2/1 to ½. The feed stock or feed mixture is obtained by adding the required amounts of propionic acid and formaldehyde to the recycle mixture of propionic acid and formaldehyde, to maintain the desired proportions. Preferred concentration of water in the reactor (including water during the reaction) is at least 3 (wt) % water of the reactor contents, including the $C_6$ to $C_{12}$ hydrocarbon.

The reaction takes place over a wide temperature range; temperatures in the range of about 280° C. to about 500° C. are satisfactory. Desirable and advantageous results are obtained by operating with temperatures in the range of about 280° C. to about 350° C. The process is normally run at atmospheric pressure, although higher or lower pressures can be used.

The space velocity of the vaporized feed mixture over the catalyst may be varied over wide limits. Space velocity figures in this specification are based on the total number of moles of materials entering the catalyst zone. Total moles are multiplied by the volume of a mole of an ideal gas at 0° C. and one atmosphere (22.4 liters/mole), to obtain the total volume. A space velocity in the range from about 100 liters per hour per liter of catalyst to about 1000 liters per hour per liter of catalyst is preferred.

Any of the various formaldehyde containing materials may be used, such as formalin, methanolic formaldehyde solution, paraformaldehyde, and trioxane.

The reactor effluent stream contains water of reaction, one mole of water for each mole of methacrylic acid produced. In a preferred method of operation, to separate the water from the propionic acid and methacrylic acid, the $C_6$ to $C_{12}$ hydrocarbon acts as an entrainer in the reactor effluent to prevent or break the water-propionic acid azeotrope upon distillation. The resulting entrainer can be any hydrocarbon capable of azeotroping with water and not forming a multi-component azeotrope with acid, as one of the components. Suitable entrainers include aliphatic saturated hydrocarbons of 6 to 8 carbon atoms such as n-hexane, n-heptane and n-octane, including their isomers, as well as benzene, o-, m-, or p- xylenes and toluene. n-Heptane is preferred.

An element of the preferred process of the invention is distillation of the reactor effluent stream under process conditions wherein concentration of 60–90 (wt) % of the unreacted formaldehyde and 25–70 (wt) % of unreacted propionic acid entering the distillation column are removed by a side-draw from the central part comprising from 10% to 90% of the theoretical trays of the distillation column for recycle to the synthesis reactor. The distillation column overhead consists of water, the hydrocarbon entrainer, comprising a $C_6$ to $C_{12}$ hydrocarbon, a small amount of formaldehyde and a trace of propionic acid. The distillation column bottoms contain methacrylic acid, propionic acid and the heavy by-products of the methacrylic acid synthesis reaction. Typical distillation column conditions are:

| Column Temperatures | |
|---|---|
| Overhead, °F. | 160°–175° |
| Side-Draw, °F. | 210°–250° |
| Bottoms, °F. | 285°–315° |
| Column Pressure, Atm. | 1 |

The primary purpose of the reactor effluent distillation tower is to remove water from the methacrylic acid synthesis reactor effluent. The overhead from this tower, consisting of formaldehyde, water, the entrainer and a small amount of propionic acid, is sent to a formaldehyde recovery and dehydration section. There, aqueous formaldehyde is reacted with an alcohol, preferably 2-ethyl-1-hexanol (2-EH) forming 2-ethylhexyl hemiformal, which is then dried. The dry hemiformal is subsequently thermally cracked liberating dry formaldehyde for recycle to the reaction section.

Introduction of a $C_6$ to $C_{12}$ hydrocarbon into the reactor also serves to prevent or break the binary azeotropes which otherwise can form. n-Heptane, as an example, upon introduction into the reactor serves to prevent or break the propionic acid-water azeotrope (BP 210° F.) with a lower boiling n-heptane-water azeotrope (BP 174.6° F). Upon distillation with no n-heptane present, propionic acid would be carried overhead from the effluent distillation column in substantial amounts. The propionic acid-water azeotrope is 17.8 (wt) % propionic acid.

In a preferred method of operation, the reactor effluent distillation tower separates water from the methacrylic acid synthesis reactor effluent and separates a substantial proportion of unreacted propionic acid and the greater proportion of unreacted formaldehyde from the synthesis reactor effluent wherein the resulting sidedraw stream of propionic acid and formaldehyde taken from the effluent contains no more than about 50 (wt) % water and methacrylic acid, the major portion of the water present in the reactor effluent being carried overhead in the form of the n-heptane-water azeotrope.

In a typical example of the method of operation, the effluent distillation tower consisted of a 40-tray two-inch vacuum jacket Oldershaw column equipped with a forced convection reboiler and a downflow condenser. Thermowells and sample taps were provided on every fifth tray of which several sample taps functioned as feed or product removal taps.

Surprisingly, it was found that under the conditions of introduction of a suitable hydrocarbon into the effluent distillation column at temperatures of from approximately 160° F. to 315° F. at one atmosphere over the length of the distillation column, high concentrations of unreacted propionic acid and unreacted formaldehyde occurred within the column at certain tray levels, permitting removal of the unreacted propionic acid and unreacted formaldehyde from the distillation column. The sidestream so removed from the distillation column can contain as much as 60-95 (wt) % of the unreacted formaldehyde and 10-70 (wt) % of the unreacted propionic acid contained in the synthesis reactor effluent. The sidestream can contain as much as a total of 50 (wt) % water and methacrylic acid.

Surprisingly, it has also been found that control of the water content of the sidestream can be obtained by control of the ratio of hydrocarbon to water in the column feed. This concentration ratio is dependent upon synthesis reactor operating conditions, in particular, the propionic acid/formaldehyde mole feed ratio to the reactor, the extent of formaldehyde conversion, the resulting water make in the reactor, the water concentration in the reactor feed, and $C_6$ to $C_{12}$ hydrocarbon concentration.

Since recovery of the unreacted formaldehyde and the hydrocarbon is necessary for the economic aspects of the process, the unreacted formaldehyde/water/hydrocarbon stream taken as overhead from the sidedraw distillation column is further processed to recover the formaldehyde and hydrocarbon. The formaldehyde is recovered by forming a hemiacetal with an alcohol selected from the group consisting of 2-ethylhexanol, cyclohexanol and other commercially available heavy alcohols. 2-Ethylhexanol is preferred. The hemiacetal, after removal of the water, is distilled to break the hemiacetal by heat to obtain the formaldehyde. The alcohol is removed as bottoms from the distillation column and recycled to reform the hemiacetal. The formaldehyde and hydrocarbon are recycled to the reactor or can be recovered separately.

The invention comprises a method of reacting in vapor phase a saturated aliphatic monocarboxylic acid compound and a formaldehyde compound, the reaction product stream comprising unreacted saturated aliphatic monocarboxylic acid compound, unreacted formaldehyde compound, alpha, beta-ethylenically unsaturated aliphatic monocarboxylic acid compound of one more carbon atom than the starting saturated aliphatic monocarboxylic acid compound and water. The process comprises adding to the reactor a $C_6$ to $C_{12}$ hydrocarbon which is a substantially non-reactive compound capable of breaking or preventing the formation of a water azeotrope of said saturated aliphatic carboxylic acid compound. In a preferred method, the reaction product is fractionally distilled with the substantially non-reactive compound under conditions whereby (1) a major proportion of ethylenically unsaturated monocarboxylic acid compound remains in the bottom of the distillation column, (2) a major portion of the water, a portion of the formaldehyde compound and a major portion of the compound capable of breaking or preventing the formation of said azeotrope are removed overhead and (3) a side stream is removed below the top of the distillation column comprising water, a major portion of formaldehyde and a substantial portion of saturated aliphatic monocarboxylic acid.

Specifically, the invention comprises a method of reacting propionic acid and formaldehyde to prepare methacrylic acid and water in an improved yield. In a preferred mode, the reaction products are fractionally distilled with $C_6$ to $C_{12}$ hydrocarbon which acts as an entrainer and unreacted propionic acid and unreacted formaldehyde are removed in a sidedraw stream.

Embodiments of the process of the present invention can be found in the following examples. These embodiments and examples are presented for purposes of illustration only and are not intended to limit the scope of the invention.

EXAMPLE I

The reactor system consisted of a 1 inch O.D. ×0.834 inch I.D.×6 foot heated Inconel tube equipped with a 0.25 inch O.D. thermowell. The catalyst zone was typically 4 feet in length and typically contains 200 gms of catalyst. Thermocouples inserted into the thermowell measured and controlled temperature at 6 inch intervals. The feed system was designed to handle a propionic acid paraformaldehyde slurry. The slurry was pumped to a vaporizer in which the paraformaldehyde was thermally decomposed to monomeric formaldehyde at 400° F. This system allowed the use of lower reactor temperatures than a feed system using trioxane and propionic acid since trioxane does not completely decompose to monomeric formaldehyde below a temperature of 750° F.

Catalyst, 143.1 g., was cesium phosphate ($Cs_3PO_4$) on silica gel, prepared by coforming. Anion (on phosphorus) catalyst loading was 1350 ppm. Cation catalyst loading as 17,000 ppm. The catalyst was regenerated after 2 days on feed at a temperature of 700° F. for a period of 48 hours.

Details of the reaction were: days on feed 3.2; reactor temperature 700° F; reactor pressure 20.0 psig, propionic acid formaldehyde molar feed ratio 1.55:1.

Three runs were made injecting n-heptane into the reactor and compared with a control with no heptane. Conditions of the separate runs and results are in Table I. Improvement in yield of methacrylic acid in the presence of n-heptane ranged from 4.1% (27.4–26.3/26.6×100) to 15.2% (30.3–26.3/26.3×100) as follows:

TABLE I

| Run No. | 184 | 182 | 183 | 185 |
|---|---|---|---|---|
| Conditions | | | | |
| Contact Time, Sec. | 13.4 | 13.9 | 13.8 | 14.8 |
| WHSV, 1/hr | 1.44 | 1.35 | 1.46 | 1.40 |
| Diluent: $N_2$, Mole % | 2.3 | 2.8 | 2.4 | 2.7 |
| Diluent: $H_2O$, wt % | 0.9 | 0.6 | 0.8 | 0.8 |
| Hydrocarbon: $C_7$, Mole % | 0.0 | 15.6 | 5.8 | 5.9 |
| Results | | | | |
| Conversion, % | 33.6 | 31.8 | 31.4 | 33.1 |
| Selectivity, Mole % | 78.4 | 95.3 | 87.2 | 83.0 |
| Yield, Mole % | 26.3 | 30.3 | 27.4 | 27.5 |

Note: Conversion, selectivity and yield are based on propionic acid.

EXAMPLE II

The following example illustrates that removal of water by distillation of reactor effluent containing a $C_6$ to $C_{12}$ hydrocarbon is facilitated by presence of the hydrocarbon. Over 90% of the water is removed as overhead.

Into a 2" vacuum jacketed Oldershaw distillation column containing 30 trays and 22 inches of 0.16" Pro Pack 316 S.S. packing at the top, equivalent to about 10 to 20 theoretical trays, 1212.9 g/hr was fed at Tray No. 8 of simulated methacrylic acid (MA) reactor effluent having the following composition of formaldehyde (FA), water ($H_2O$), propionic acid (PA) and n-heptane ($C_7$),

| | FA | $H_2O$ | PA | MA | $C_7$ |
|---|---|---|---|---|---|
| wt % | 9.11 | 3.69 | 40.37 | 16.05 | 30.51 |
| mole % | 19.1 | 14 | 35 | 12.1 | 19.8 |

Also incorporated into the feed to prevent MA polymerization in the tower bottoms was 1000 ppm p-benzoquinone and 500 ppm phenothiazine. In addition 4500–5000 ppm oxygen (as 50 vol.% with nitrogen) was sparged into the reboiler of the column. All levels are based on MA in the feed.

As a control, actual pilot-plant reactor effluent containing small amounts of the by-products was fed to the reactor effluent column under nearly identical condition. Additional inhibitor was required to keep the system MA polymer free. The pilot plant reactor effluent had the composition of by-products described below;

| | (wt) % |
|---|---|
| 3-Pentanone | 0.034 |
| Isobutyric Acid | 0.05 |
| 2,5-Dimethylcyclopentenone | 0.013 |
| 2,2,4-Trimethylbutyrolactone | 0.003 |

An inhibitor package of 1100 ppm p-benzoquinone, 1100 ppm t-butylcatechol and 550 ppm phenothiozine together with an $O_2$ addition rate of 10,000 ppm $O_2$ (all based on MA fed to the column) allowed operation with no visible evidence of MA polymers.

The column was operated at atmospheric pressure with the temperature at various locations in the column as follows:

| Column Bottoms | Feed Tray No. 8 | Sidedraw Tray No. 13 | Column Overhead |
|---|---|---|---|
| 296° F. | 264° F. | 220° F. | 169° F. |

The compositions and takeoff rates for the column bottoms, sidedraw (Tray No. 18) and overhead are given below.

| Location | Rate (g/HR) | Composition Analysis (wt) % | | | | |
|---|---|---|---|---|---|---|
| | | FA | $H_2O$ | PA | MA | $C_7$ |
| Overhead Aqueous | 59.9 | 25.69 | 72.60 | 1.71 | — | ~0 |
| Organic | 373.8 | — | — | — | — | ~100 |
| Sidedraw | 238.3 | 41.22 | 3.50 | 52.12 | 2.36 | 0.8 |
| Bottoms | 553.6 | <0.01 | 0.07 | 65.23 | 34.69 | ~0 |
| | 1225.6 g | (101.0% Theory) | | | | |

The wt. % of FA and PA in the sidedraw stream correspond to 88.9% of the FA fed to the column (unreacted FA) and 25.4% the PA fed to the column (unreacted PA).

What is claimed is:

1. The process of producing an alpha-, betaethylenically unsaturated monocarboxylic acid compound which comprises the aldol-type condensation of a saturated aliphatic monocarboxylic acid compound and formaldehyde compound under vapor phase conditions in the presence of a hydrocarbon of 6 to 12 carbon atoms and a solid catalyst.

2. The process of claim 1 wherein said catalyst is a silica catalyst comprising a cation of a Group I or Group II metal and a silica support.

3. The process of claim 1 wherein said hydrocarbon of 6 to 12 carbon atoms is a substantially non-reactive, water-immiscible hydrocarbon.

4. The process of claim 3 wherein said hydrocarbon forms a water azeotrope having a boiling point of no more than 95° C. at 1 atmosphere pressure.

5. The process of claim 3 wherein said hydrocarbon is selected from the group consisting of n-hexane, n-heptane, n-octanes, n-nonanes, n-decanes and their isomers, aromatic hydrocarbons and cycloalkanes of up to 12 carbon atoms, and mixtures thereof.

* * * * *